United States Patent [19]

Smith

[11] Patent Number: 4,879,113

[45] Date of Patent: Nov. 7, 1989

[54] VACCINE FOR IMMUNOLOGICALLY MEDIATED NUTRITIONAL DISTURBANCES ASSOCIATED WITH PLANT PROTEIN ANTIGENS

[76] Inventor: Clyde K. Smith, 3743 Bay Shore Dr., Sturgeon Bay, Wis. 54235

[21] Appl. No.: 114,082

[22] Filed: Oct. 27, 1987

[51] Int. Cl.$^4$ .................... A61K 39/00; A61K 39/12; A61K 39/02

[52] U.S. Cl. ........................................ 424/88; 424/89; 424/91; 424/92

[58] Field of Search ...................... 424/88, 92, 91, 89

[56] References Cited

PUBLICATIONS

Barratt et al, "Immunologically Mediated Nutritional Disturbances Associated With Soya Protein Antigens", Proc. Nutr. Soc., vol. 38, pp. 143-150, 1979.

Challocombe et al, "Systemic Tolerance and Secretory Immunity Offer Oral Immunization", J. Exp. Med., vol. 152, pp. 1459-1472, 1980.

Zoppi et al, "Diet and Antibody Response to Vaccinations in Healthy Infants", The Lancet, July 12, 1983, pp. 11-14.

Effect of Soya Protein on Digestive Enzymes, Gut Hormone, and Anti-Soya Antibody Plasma Levels in the Preruminant Calf, Guilloteau, et al., Reprod. Nutr. Develop. 26 (2B), 717-728, 1986.

Immunologically Mediated Nutritional Disturbances Associated with Soya-Protein Antigens, Proc. Nutr. Soc. (1979), 38, 143.

Barratt et al., Immunoglobulin Classes Implicated in Intestinal Disturbances of Calves Associated with Soya Protein Antigens, The Journal of Immunology, (1979), 123 (2):676-680.

Tomsai, Oral Tolerance, *Transplantation*, vol. 29, No. 5, 353-356 (1980).

Challacombe et al., Systemic Tolerance and Secretory Immunity After Oral Immunization, *J. Exp. Med.*, vol. 152, 1459-1472 (Dec. 1980).

Walker, et al., The Effect of Pancreatic Duct Ligation on the Breakdown of Antigen an Antigen-Antibody Complexes on the Intestinal Surface, *Gastroenterology*, vol. 69, No. 6, 1223-1229 (1975).

Andre et al., A Mechanism for the Induction of Immunological Tolerance by Antigen Feeding: Antigen-Antibody Complexes, *J. Exp. Med.*, 142: 1509-1519 (1975).

McGhee et al., The Secretory Immune System, Anal. of the New York Academy of Sciences, vol. 409, pp. 593, et seq., 673 et seq., 650 et seq., and 724, et seq.

Kirk-Othmer, *Encyclopedia of Chemical Technology*, 3d Ed., vol. 11, pp. 198-207, vol. 19, pp. 332-341; and vol. 21, pp. 432-442; John Wiley & Sons (1980).

*Primary Examiner*—Margaret Moskowitz
*Assistant Examiner*—Abdel A. Mohamed
*Attorney, Agent, or Firm*—Mueller and Smith

[57] ABSTRACT

The present invention is directed to overcoming immunologically mediated nutritional disturbances in pre-ruminant associated with plant protein antigens and to a vaccine therefor. In accordance with the present invention bovine can be fed dietary plant protein, such as soy protein, after being vaccinated in accordance with the vaccine disclosed herein. The regimen comprises administering orally or parenterally to the pre-ruminant bovine an effective amount of the plant protein which is later to be fed to the bovine. After a selected suitable time interval, the bovine then is parenterally administered a second effective amount of said plant protein, thereby permitting the bovine to be fed the dietary plant protein of the vaccine.

24 Claims, No Drawings

VACCINE FOR IMMUNOLOGICALLY MEDIATED NUTRITIONAL DISTURBANCES ASSOCIATED WITH PLANT PROTEIN ANTIGENS

BACKGROUND OF THE INVENTION

The present invention relates to nutritional disturbances in bovine associated with ingestion of plant protein antigens and more particularly to vaccines for bovine effective for overcoming such disturbances of immunological origin.

A relationship between the poor performance of pre-ruminant fed on milk replacer having soy protein as a major ingredient and a component of the soy protein that is antigenic to the animal has been demonstrated through the production of high titers of antibody to the soy protein in the blood serum. Nutritional disturbances are not manifested on the first introduction of soy protein into the bovine diet. The animals exhibit such changes upon second and subsequent feedings of soy protein which generally coincides with demonstrable serum antibody, strongly leading researchers in the field to suggest an immunological basis for these interferences with physiological function.

It is believed that sufficient intact macromolecules can be absorbed to induce both local and systemic immune responses. This state of immunity may manifest itself in a protective function, or a destructive function being mediated as a hypersensitivity reaction. Some authors have suggested that hot aqueous ethanol extraction of soybean meal is effective in reducing the apparent antigenic nature of the product (Guilloteau et al., "Effective Soya Protein on Digestive Enzymes, Gut Hormone and Anti-Soya Antibody Plasma Levels in the Pre-Ruminant Calf", *Reprod. Nutr. Develop.*, 26 (2B), 717–728, 1986), though most investigators report that the harmful antigen clearly survives such extraction technique.

The intestinal mucosa of pre-ruminant bovine is affected by a variety of foreign substances, many of which, under the appropriate stimulation, can act as antigens. Ingested foodstuffs are among such foreign substances which can evoke an adverse immunologic reaction. Local synthesis and secretion of immunoglobulin within the intestinal mucous membrane primarily is responsible for the prevention of the absorption of antigen. The major immune response to dietary soya protein antigen, for example, in the young calf has been demonstrated to be an IgG1 precipitant capable of fixing complement (C). The antigen-antibody reaction that occurs in the lamina propia of the intestinal tract results in hemorrhage, edema, and monocellular infiltration. The villi of the intestine become shorter and broader, thus decreasing the absorptive area and the efficiency of digestion. In some instances, the calf will develop a hypersensitive reaction to the soy protein. These calves usually exhibit a selective anorexia to soy milk and do not gain weight. A good discussion of this subject can be found by Barratt et al. "Immunologically Mediated Nutritional Disturbances Associated with Soya-Protein Antigens", *Proc. Nutr. Soc.* (1979), 38, 143, and Barratt et al., "Immunoglobulin Classes Implicated in Intestinal Disturbances of Calves Associated with Soya Protein Antigens", *The Journal of Immunology*, (1979) 123 (2): 676–680.

BROAD STATEMENT OF THE INVENTION

The present invention is directed to overcoming immunologically mediated nutritional disturbances in pre-ruminant associated with plant protein antigens and to a vaccine therefor. In accordance with the present invention bovine can be fed dietary plant protein, such as soy protein, after being vaccinated in accordance with the vaccine disclosed herein. The regimen comprises administering orally or parenterally to the pre-ruminant bovine an effective amount of the plant protein which is later to be fed to the bovine. After a selected suitable time interval, the bovine then is parenterally dministered a second effective amount of said plant protein, thereby permitting the bovine to be fed the dietary plant protein of the vaccine.

Advantages of the present invention include the ability to effectively immunize the calves with plant protein to stablish a state of systemic immunologic tolerance. Another advantage is that the vaccine is cost effective and in plentiful supply. A further advantage is that calves vaccinated in accordance with the present invention which then are fed a milk replacer formula containing the plant protein as a major protein source exhibit improved feed efficiencies compared to unvaccinated calves fed on the same formula. These and other advantages will be readily apparent to those skilled in the art based upon the disclosure contained herein.

DETAILED DESCRIPTION OF THE INVENTION

In accordance with the precepts of the present invention, pre-ruminant bovine or calves are effectively immunized with plant protein to establish a state of systemic immmunologic tolerance. That such immunologic tolerance can be achieved by use of the plant protein source itself is not without precedent. In this regard, reference is made to Tomasi, "Oral Tolerance", *Transplantation*, Vol. 19, No. 5, 353–356 (1980), and Challacombe et al., "Systemic Tolerance and Secretory Immunity After Oral Immunization", *J. Exp. Med.*, Vol. 152, 1459–1472 (Dec. 1980). Further, Walker et al., "The Effect of Pancreatic Duct Ligation on the Breakdown of Antigen and Antigen-Antibody Complexes on the Intestinal Surface", *Gastroenterology*, Vol. 69, No. 6, 1223–1229 (1975), report the ability of an immunized gut to resist the penetration of proteins and the subsequent digestion of the protein in the gut. Andre et al., "A Mechanism for the Induction of Immunological Tolerance by Antigen Feeding: Antigen-Antobody Complexes", *J. Exp. Med.*, 142: 1509–1519 (1975), report that the intra-gastric immunized mice were tolerant to parenteral challenge and they produced strong tolerance factor in the serum.

As proffered by Tomasi, supra, such systemic tolerance can be visualized as a defense against the development of certain hypersensitivity in autoimmune diseases by preventing reactions to antigens which have escaped immune exclusion. Such thesis continues that sensitization in atopic subjects may occur in early life when the secretory immune system is immature and allows access of potential allegens to the animal's system. In this regard, see McGhee et al., *The Secretory Immune System*, Annal. of the New York Academy of Sciences, Vol. 409, especially pp. 593 et seq, 637 et seq, 650 et seq, and 724 et seq. It is possible, then, that the continued absorption of large amounts of orally ingested antigens (plant protein) could lead to the production of immune complexes or possibly to antibodies which cross-react with self-tissue components, both of which lead to autoimmune phenomena. In this regard, it will be remembered that researchers have reported that the initial ingestion of plant protein causes no apparent difficulties in the animal. It is the second and subsequent ingestion of the plant protein source that evokes the nutritional disturbances associated therewith.

The vaccination regimen determined for effectively immunizing bovine with plant protein involves the administration of the plant protein itself twice. The initial administration desirably should take place when the calf is about 3–8 weeks in age. Prior to such initial vaccination, the calf should be fed conventional cow's milk formula. When the initial parenteral administration of plant protein is via the subcutaneous route, there is a high incidence of abcesses at the initial injection site. Thus, the initial plant protein vaccination preferably is oral. About 20 g. of the plant protein can be orally taken by the calf. When parenteral administration is the method of choice for the initial vaccination, about 2cc of a 5 wt-% solution of plant protein can be utilized. As noted in the literature, this initial administration of plant protein causes no apparent nutritional disturbances in the calves.

After the initial vaccination, the calves again are returned to their conventional milk formula diet for about 10–14 days. At this point in time, the calves are parenterally dministered about 2cc of a 5% solution of plant protein. While such parenteral administraton may be subcutaneous intradermal, or intraperitoneal, for example, data has indicated that improved feed efficiences are associated with intraperitoneal administration of the second or booster vaccination. This injection acts as a booster vaccination to the immune system of the mucosal surfaces and establishes a systemic tolerance to the plant protein antigens in the calf. Thereafter, the calves may be fed milk that contains a protein of plant origin as a major protein component for the remaindeer of the feeding period.

The plant protein vaccine is a suspension or solution utilizing water or other suitable solvent to suspend or carry the plant protein source. The oral vaccine additionally can contain conventional milk protein derived from dried skim milk, whey protein concentrate, whey powder, or the like, balanced nutritionally to supply vitamins, minerals, and trace elements as well as blended with animal and vegetable fat emulsifiers.

A variety of vegetable protein sources are appropriate for use in formulating milk replacers and for use in formulating the vaccine of the present invention. Such vegetable protein sources include, for example, soya, linseed, corn, cottonseed, peanut, sunflower, and the like and mixtures thereof. Leaf-protein concentrates also can be utilized. In this regard, it will be appreciated that the composition of the dietary vegetable protein formula to be fed to the calves determines the composition of the vaccine. Further information regarding vegetable or plant protein sources can be found in Kirk-Othmer, *Encyclopedia of Chemical Technology*, 3d Ed., Vol. 11, pp 198–207; Vol. 19, pp 332–341; and Vol. 21, pp 432–442, John Wiley & Sons (1980).

The following examples show how the present invention has been practiced but should not be construed as limiting. In this application, all citations are expressly incorporated herein by reference.

EXAMPLES

Example 1

This comparative example confirms the literature that calves are unable to utilize soy protein in the diet due to an immunologically mediated intestinal disturbance. 120 calves were fed a conventional milk protein formula for their initial 28 days following birth. Thereafter, a soy milk formula was gradually introduced into their diet as follows:

TABLE 1

| Age of Calves (days) | % Soy Protein Formula | % Milk Protein Formula |
| --- | --- | --- |
| 1 | 0 | 100 |
| 28 | 25 | 75 |
| 33 | 50 | 50 |
| 38 | 75 | 25 |
| 43 | 100 | 0 |
| 70 | 0 | 100 |

At ten weeks of age, many of the calves were not eating the soy protein formula and were not gaining weight as expected when compared with the 240 milk protein fed calves. The soy formula fed calves also exhibited severe intestinal disturbances. All of the calves were returned to the milk protein formula at 10 weeks of age.

Example 2

In this example 60 calves were divided into three groups. The first group of 20 calves were vaccinated subcutaneously with 2 cc of isolated soy protein A (isolated soy protein, typical analysis: 91.5% protein, 6.0% moisture, a 5% fat, 4.5% ash, 0.5% fiber, pH of 7.0; Milk Specialties Company), the second group vaccinated subcutaneously with 2 cc of soy protein concentrate B (specifications: 67–69% protein, 0.1% min. fat, 6.0% max. ash, 4–6% moisture, 4.0% max. fiber, pH of 6.6–6.9; Milk Specialties Company), and the third group was a control which received no innoculation. The first vaccination took place when the calves were 21 days old. A second set of vaccinations was administered to the first two groups at 35 days of age.

All of the calves were fed a conventional milk formula for their initial 6 weeks followed by a 50:50 (st) mixture of soy protein A or B for 10 days, and finally the soy protein A or B for the remaining 7½ weeks of the test. The control animals were fed the milk formula through the duration of the test. The weight gain of the three groups of calves was recorded as follows:

TABLE 2

| | Calf Weight (lb)* | | |
| --- | --- | --- | --- |
| Age (weeks) | Soy Protein Group A | Soy Protein Group B | Control Group |
| 10 | 270 | 260 | 240 |
| 11 | 300 | 285 | 275 |
| 13 | 315 | 310 | 305 |
| 15 | 335 | 330 | 325 |

*Average of 20 calves.

The above-tabulated results demonstrate that both immunized groups of calves completed the feeding period and gained weight at least as well as did the control group. There was a high incidence (about 50%) of abcesses at the site of the injection of the soy protein. Thus, while the immunization regimen is demonstrated to be effective, another means of delivery appeared to be needed.

Example 3

In this example, three groups of 19 calves each were vaccinated using an oral immunization followed by either a subcutaneous, intraperitoneal, or intradermal route. The following vaccination regimen was used.

TABLE 3

Initial Vaccination: Two feedings of Soy Protein A at 9 weeks of age-All Groups.
 Booster Vaccination: 11 weeks of Age
 Group I: 2cc of a 5% solution of Soy Protein A subcutaneously
 Group II: 2cc of a 5% solution of Soy Protein A intraperitoneally
 Group III: 2cc of a 5% solution of Soy Protein A intradermally.

Following the booster injection, a soy milk formula was gradually introduced into their diet as follows:

TABLE 4

| Time After Booster (days) | % Soy Protein Formula* | % Milk Protein Formula* |
|---|---|---|
| 0 | 25 | 75 |
| 1 | 50 | 50 |
| 3 | 75 | 25 |
| 4–28 | 100 | 0 |

*3 feedings

Starting with the calves at 11 weeks of age when the booster vaccination was administered, the calves were weighed and compared to an identical control group that was fed a dairy milk diet and was not vaccinated.

TABLE 5

| Age Weeks | Weeks on Soy Diet | Calves Weight (lbs, Av. of 10) | | | |
|---|---|---|---|---|---|
| | | Control | Group I | Group II | Group III |
| 11 | 0 | 275 | 280 | 290 | 280 |
| 13 | 2 | 310 | 310 | 315 | 310 |
| 15 | 4 | 325 | 325 | 335 | 325 |

These results demonstrate the efficacy of the vaccination regimen of the present invention. After 7½ wekks on the soy protein diet, the calves were marketed. The Group II (intraperitoneal booster) calves weighed an average of 15 pounds dressed weight per calf more than the control calves.

Example 4

Two groups of 120 calves each were fed Soy Protein A formula two times (20 g. each feeding) at 21 days of age. One group of 120 calves was vaccinated intradermally (2cc) and the other group was vaccinated intraperitoneally (2cc) 14 days after the oral vaccination. Both groups thereafter were fed the Soy Protein A formula for 10 weeks. The results of these two groups of calves along with a control group (milk formula feed only) are set forth below.

TABLE 6

| Variable | Control | Intradermal Injection Group | Intraperitoneal Injection Group |
|---|---|---|---|
| Number of Calves | 120 | 120 | 120 |
| Initial Weight (lb) | 90 | 90 | 90 |
| Finished Weight (lb) | 390.85 | 384 | 394.96 |
| Feed Weight/ Calf Weight Gain | 1.712 | 1.747 | 1.686 |

These results demonstrate that the calves which were vaccinated and fed with the plant protein source achieved a weight gain at least as good as did the control group fed on conventional milk formula. Also, the feed efficiency (ratio of feed to weight gain of the calf) of the vaccinated calves was about the same for the intradermal group as the control group and slightly less for the intraperitoneal group. The preference for the intraperitoneal injection route for the booster injection is substantiated by these data which show both higher weight gains and lower feed efficiencies compared to the control group and the intradermal group.

I claim:

1. A method for suppressing immunologically-mediated nutritional disturbances associated with pre-ruminant bovine ingestion of dietary plant protein, which comprises the steps of:
 (a) administering to said pre-ruminant bovine said plant protein in an amount effective to prevent a nutritional disturbance in said pre-ruminant bovine due to the formation of an immune response to the dietary plant protein; and
 (b) parenterally administering to said pre-ruminant bovine of step (a) again a second effective amount of said plant protein, there being a selected suitable time interval between said two administrations.

2. The method of claim 1 wherein step (a) comprises oral administering, parenteral administering, or a combination thereof.

3. The method of claim 2 wherein step (a) comprises oral administering.

4. The method of claim 1 wherein said parenteral administering of step (b) is selected from intradermal or intraperitoneal administering.

5. The method of claim 4 wherein step (b) comprises intraperitoneal administering.

6. The method of claim 3 wherein step (b) comprises intraperitoneal administering.

7. The method of claim 1 wherein said administering step (a) is accomplished when said bovine is between about 3 and 8 weeks in age.

8. The method of claim 1 wherein said selected suitable time interval ranges from between about 10 and 14 days.

9. The method of claim 3 wherein said effective amount comprises about 20 grams.

10. The method of claim 4 wherein said second effective amount comprises about 2 cc of a 5 wt-% solution of said plant protein.

11. A method for permitting pre-ruminant bovine to be fed dietary plant protein which comprises the steps of:
 (a) administering to said pre-ruminant bovine said plant protein in an amount effective to prevent a nutritional disturbance in said pre-ruminant bovine due to the formation of an immune response to the dietary plant protein;
 (b) parenterally administering to said pre-ruminant bovine of step (a) again a second effective amount of said plant protein, there being a selected suitable time interval between said two administrations; and (c) thereafter feeding said bovine a diet comprising said plant protein administered in steps (a) and (b).

12. The method of claim 11 wherein step (a) comprises oral administering, parenteral administering, or a combination thereof.

13. The method of claim 12 wherein step (a) comprises oral administering.

14. The method of claim 11 wherein said parenteral administering of step (b) is selected from intradermal or intraperitoneal administering.

15. The method of claim 14 wherein step (b) comprises intraperitoneal administering.

16. The method of claim 13 wherein step (b) comprises intraperitoneal administering.

17. The method of claim 11 wherein said administering step (a) is accomplished when said bovine is between about 3 and 8 weeks in age.

18. The method of claim 11 wherein said selected suitable time interval ranges from between about 10 and 14 days.

19. The method of claim 13 wherein said effective amount comprises about 20 grams.

20. The method of claim 14 wherein said second effective amount comprises about 2 cc of a 5 wt-% solution of said plant protein.

21. The method of claim 1 wherein the source for said dietary plant protein is selected from the group consisting of soya, linseed, corn, cottonseed, peanut, and sunflower sources and mixtures thereof.

22. The method of claim 21 wherein said dietary plant protein comprises soya plant protein.

23. The method of claim 11 wherein said dietary plant protein is selected from the group consisting of soya, linseed, corn, cottonseed, peanut, and sunflower sources and mixtures thereof.

24. The method of claim 23 wherein said dietary plant protein comprises soya plant protein.

* * * * *